United States Patent [19]

Myrick et al.

[11] 4,212,939
[45] * Jul. 15, 1980

[54] SUBSTRATE SOLUTION FOR CARBOXYLIC ESTER HYDROLASE DETERMINATION

[75] Inventors: James E. Myrick, Houston, Tex.; Leo M. Hall, Birmingham, Ala.

[73] Assignee: The University of Alabama, Birmingham, Ala.

[*] Notice: The portion of the term of this patent subsequent to May 10, 1994, has been disclaimed.

[21] Appl. No.: 854,046

[22] Filed: Nov. 22, 1977

Related U.S. Application Data

[60] Division of Ser. No. 775,470, Mar. 8, 1977, abandoned, and a continuation-in-part of Ser. No. 615,559, Sep. 22, 1975, said Ser. No. 775,470, is a continuation-in-part of Ser. No. 615,559, Sep. 22, 1975, Pat. No. 4,022,667.

[51] Int. Cl.$^2$ .................... G01N 31/14; G01N 31/22
[52] U.S. Cl. ........................................ 435/19; 435/26; 252/408
[58] Field of Search .................. 195/99, 103.5 R; 23/230 B; 252/408 R; 435/26, 19

[56] References Cited

U.S. PATENT DOCUMENTS

4,022,667    5/1977    Myrick et al. ................ 195/103.5 R

OTHER PUBLICATIONS

*The Merck Index*, 8th Ed., Stecher (Ed)., Merck & Co., Inc., 1968 Rahway, N.J., p. 360.
Brockerhoff, Biochim. Biophys. Acta, 212, (1970), pp. 92-101.
Whitaker, Clinica Chimica Acta, 44 (1973), pp. 133-138.
Gomori, *J. Lab. & Clin. Med.*, 42 (1953), pp. 445-453.

*Primary Examiner*—Esther M. Kepplinger
*Attorney, Agent, or Firm*—Oblon, Fisher, Spivak, McClelland & Maier

[57] ABSTRACT

A clear, stable aqueous reagent solution comprising a mixture of a water insoluble vinyl ester of an alkyl, alkenyl, or alkyl-aryl carboxylic acid, nonionic detergents, inorganic salts, enzyme activators, and a buffer, which when combined with a suitable acetaldehyde detection system is useful for the analysis of the action of certain carboxylic ester hydrolases.

13 Claims, No Drawings

SUBSTRATE SOLUTION FOR CARBOXYLIC ESTER HYDROLASE DETERMINATION

This is a division of application Ser. No. 775,470 filed Mar. 8, 1977, now abandoned, which in turn is a CIP of application Ser. No. 615,559, filed Sept. 22, 1975, now U.S. Pat. No. 4,022,667.

BACKGROUND OF THE INVENTION

1. Field of the Invention

This invention relates to a method for the detection and measurement of carboxylic acid ester hydrolases.

2. Description of the Prior Art

There are three known methods that may be undertaken for the measurement of carboxylic ester hydrolases. They are as follows:

1. Turbidimetric Methods. These methods are designed to measure esterases which act on insoluble esters present in an emulsified form (aided by certain emulsifiers) of sufficient dilution at the time of assay so that optical measurements can be made thereon. The principle of operation lies in the clearing effect that the products of hydrolysis, fatty acids and partial glycerides have on the turbidity of the assay solution. The most common ester used in this type of method has been glycerol trioleate either in its purified form or as olive oil. Since the clearing effect of the fatty acids depends on their ionization, these methods are only applicable in the alkaline pH range. Also, due to design differences in the light paths of different spectrophotometers what may be an acceptable wavelength in one instrument for turbidity measurements is not necessarily the best wavelength in all instruments (Vogel and Zieve, *Clinical Chemistry*, 9, 168–181 [1963]). Further, turbidimetric methods are relatively insensitive and do not show good linearity of measured activity with enzyme content, especially at high enzyme levels.

2. Measurement of Liberated Fatty Acids. The fatty acids produced after hydrolysis may be measured by a number of methods. They may be titrated after extraction, or they may be continuously titrated during the course of hydrolysis. The latter method allows a kinetic assay of an ester hydrolase to be made but is limited to the alkaline pH range and requires a special recording titrator. Color changes of an acid-base indicator may be measured as the hydrolysis progresses, theoretically yielding a very sensitive assay. However, to be applicable to a wide number of ester hydrolases with different pH optima a number of indicators are required, and it is necessary to match their pK's to the particular hydrolase to be measured as well as to the pK of any buffer present in the solution so as to obtain zero order kinetics. The sensitivity of this type of method is inversely proportional to the amount of buffer present. The liberated fatty acids may, also, be determined by a first conversion to their copper salts and subsequently measured colorimetrically. The most sensitive method involves the use of radioactive esters labeled in the acid portion. The liberated fatty acid, after separation from the unhydrolyzed ester, is counted in a suitable scintillation counter. This type of method however is very time consuming and expensive.

3. Measurement of Liberated Alcohol. Certain esters of phenols are used in this technique and the free phenolic product of hydrolysis is measured colorimetrically. This type of method allows continuous monitoring of the reaction only in the pH range in which the phenol is colored. As an extension of this method and a method of greater sensitivity is that of fluorometric analysis after coupling the liberated phenol with an azo dye. However the specificity of the phenol esters for certain hydrolases is questionable, especially the water soluble phenol esters to triglyceride lipase such as found in the pancreas. Also, pancreatic lipase has a very low specific activity even for water insoluble phenol esters. Rather than phenolic esters, other fluorometric methods utilize carboxylic acid esters of alcohols such as $\beta$-naphthol, fluorescein, or 4-methyl-umbelliferone which fluoresce after hydrolysis. These esters are, however, poor substrates for pancreatic lipase. Vinyl esters have also been used to measure hydrolases (Brockerhoff, H. *Biochimica et Biophysica Acta*, 212, 92 [1970] and Brockerhoff, H. et al, *Analytical Biochemistry*, 37, 26–31 [1970]). With these esters the OH-containing moiety is not measured, but, its isomerization product, acetaldehyde. In the Brockerhoff technique, the vinyl ester is emulsified, thus, precluding any possible optical measurements on the reaction as it progresses. Aliquots of the reaction mixture containing acetaldehyde are coupled to 3-methyl-2-benzothiazolone hydrazone, thus forming a colored product which is determined colorimetrically at 666 nm. However, the vinyl oleate which is used as a substrate is only 29.4% as effective as glycerol trioleate under the same conditions using porcine pancreatic lipase for these measurements. However, vinyl oleate is a much better substrate than the phenolic esters or the esters of the fluorescent alcohols. Significantly, Brockerhoff notes that the kinetics of his method are not linear above an absorbance of about 0.6. The Brockerhoff method, although an improvement over many of the prior art methodologies, is one that must be carried out manually and requires the preparation of several different solutions as well as a great amount of technician time.

Almost all of the methods noted above involve the use of relatively unstable reagent mixtures, especially those which require any kind of an emulsion of a water insoluble substrate. The methods which do use water soluble substrates either have an extremely low specific activity toward triglyceride lipases, or are subject to interference from ester hydrolases which act on water soluble substrates, or both. Triglyceride lipases may, also, interfere with methodologies designed to measure ester hydrolases of water soluble substrates, since the substrate specificities of many triglyceride lipases include water soluble ones as well. A common example of multiple enzyme systems of this type is blood serum or plasma, which may contain pancreatic lipase from an inflamed pancreas as well as a liver esterase. A method designed to differentiate lipase activity from that of the esterase must be highly specific for the former in order to be a reliable diagnostic tool for the detection of pancreatic inflamations. Such reagent solution must be highly sensitive to detect low levels of enzyme activity, stable upon storage for long periods of time, capable of being assayed very quickly after addition of the ester hydrolase (preferably using continuous monitoring techniques to provide for a kinetic assay), free from turbidity effects during the reaction, and economically feasible for manufacturing. A need therefore, exists for a reagent solution which displays high sensitivity, good clarity and storage stability and is capable of quickly measuring a particular ester hydrolase, e.g., triglyceride lipase, even in the presence of other types of ester hydrolases which may have different substrate specificities or other properties.

SUMMARY OF THE INVENTION

Accordingly, it is an object of this invention to provide a reagent solution for the determination of carboxylic ester hydrolase that can be made specific for a particular hydrolase even in the presence of other hydrolases.

It is a further object of this invention to provide a reagent solution for the determination of carboxylic ester hydrolases that is stable for long periods of time.

It is still a further object of this invention to provide a reagent solution for the determination of carboxylic ester hydrolases that is sensitive to low levels of enzymatic activity over short periods of time.

It is still a further object of this invention to provide a reagent solution for the determination of carboxylic acid ester hydrolases that is homogeneous and clear and allows spectrophotometric, fluorometric, or colorimetric measurements of the enzymatic reaction as it progresses, based on the extinction of a single component in the reaction medium which is stoichiometrically equivalent to the amount of ester hydrolyzed.

It is still a further object of this invention to provide a reagent solution for the determination of carboxylic acid ester hydrolases that exhibits a linear correlation of measured activity with ester hydrolase concentration.

These and other objects of the present invention can be attained by providing an aqueous reagent solution of a mixture of a vinyl ester of a carboxylic acid, a nonionic detergent, certain inorganic salts, an anionic detergent, a cationic detergent, and a buffer.

DESCRIPTION OF THE PREFERRED EMBODIMENTS

In accordance with the preferred embodiments of this invention, we prefer to carry out the analysis of carboxylic acid ester hydrolase by admixing an unknown, suspected of containing this enzyme with a reagent system wherein first a vinyl ester of a carboxylic acid is hydrolyzed by the enzyme into the carboxylic acid and unstable vinyl alcohol. As a second step, the vinyl alcohol isomerizes to acetaldehyde. This sequence of conversions is indicated diagrammatically as follows:

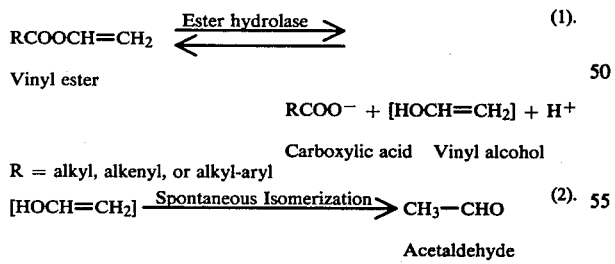

The acetaldehyde of reaction (2) may be detected by a variety of means known to the prior art. For example, enzymatic methods are illustrated below in reactions (3a) and (3b), and involve monitoring the disappearance (3a) or appearance (3b) of NADH by measuring its absorbance or fluorescence at suitable wavelengths. The velocity of reactions (3a) or (3b) may then be equated with reaction (1) when the components of the mixture are all in sufficient excess so that only the ester hydrolase activity is limiting. Chemical methods (3c) may include any nonenzymatic means for the quantitative analysis of acetaldehyde.

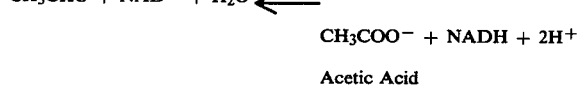

(3c) $CH_3CHO$ detected chemically.

NADH = B-dihydronicotinamide adenine dinucleotide
ADH = alcohol dehydrogenase
NAD+ = Nicotinamide adenine dinucleotide
AD = Aldehyde dehydrogenase Examples of chemical detection methods for acetaldehyde may include Schiff base forming dyes such as Basic Fuchsin which are highly colored.

The preparation of the reagent of this invention is most advantageously effected by combining two separate preparations, one a substrate-detergent blend and the other a buffer solution which may contain certain activators and stabilizers.

The substrate-detergent blend comprises a carboxylic vinyl ester substrate and one or more of a variety of nonionic detergents.

The substrate of choice depends on the specificity of the carboxylic ester hydrolase to be measured. Hydrolases which catalyze the hydrolysis of water-soluble carboxylic acid esters of natural origin more rapidly than longer chain, water-insoluble carboxylic acid esters will hydrolyze the short chain carboxylic vinyl esters more rapidly than the long chain carboxylic vinyl esters, which become more water-insoluble as the chain length increases. Hydrolases which are known to catalyze long chain carboxylic acid esters of natural origin, e.g., triglycerides, tend to catalyze the hydrolysis of long chain carboxylic vinyl esters faster than the other hydrolases. While any vinyl carboxylic acid ester can be used as a substrate, preferred substrates are those having 4 to 20 carbon atoms. These include vinyl acetate, vinyl propionate, vinyl butyrate, vinyl crotonate, vinyl valerate, vinyl hexanoate, vinyl octanoate, vinyl nonanoate, vinyl decanoate, vinyl neodecanoate, vinyl laurate, vinyl myristate, vinyl palmitate, vinyl oleate, vinyl stearate, divinyl suberate, and vinyl omega-phenyl nonanoate. Most preferred is vinyl omega-phenyl octanoate which has been prepared by a modification of the method of Catterjee, et al. (P. C. Catterjee, H. Dakshinamurty, and J. S. Aggarval, *Indian J. Technol.*, 4, 173–175 [1966]). The compounds vinyl omega-phenyl octanoate and vinyl omega-phenyl nonanoate have been synthesized for the first time. The useful range of substrate concentration is 5 to 15 mM, and the most preferred is 7 to 10 mM. The preferred substrate concentration depends partly on the Km of the enzyme for a particular substrate. For kinetic reasons a substrate concentration of about 10 times the Km is recommended.

Omega-phenyloctanoic acid (0.2 mole), vinyl acetate (1.2 mole), and mercuric acetate (2.51 moles) were combined; hydrofluoric acid, 48%, (12.24 moles) was added slowly; and the mixture was refluxed for 3 hours. After cooling, sodium acetate trihydrate (12.24 moles) was added to neutralize the HF. Excess vinyl acetate and acetic acid were removed by distillation under a water tap vacuum. The distillation proceeded at about 26° C. After cooling, the flask contents were extracted with 200 ml of petroleum ether (B.P. 30°-75° C.). The petroleum ether solution was washed with 70 ml of 4% sodium carbonate and then successively three times with 100 ml of deionized water. The organic phase was dried over anhydrous sodium sulfate. The ether solution was vacuum distilled after the addition of 200 mg of copper resinate as a polymerization inhibitor. Alternatively, hydroquinone could be used. An average yield of 75% was obtained. Omega-phenylnonanoate was prepared by a completely analogous procedure.

The most effective nonionic detergents that have been found useful in the reagent of this invention are polyoxyethylenated alcohols or polyoxylethylenenated alkylphenols and their ethers (Class 1A2 of Rosen and Goldsmith, Systematic Analysis of Surface-Active Agents, 2nd ed., Wiley-Interscience, New York, 1972). While any nonionic surfactant compound of this type which does not contain carboxylic acid ester linkages can be used as the detergent part of this detergent-substrate blend, those preferred detergents are polyoxyethylene (23) lauryl ether, polyoxyethylenated tert-octylphenol (from 7 to 40 moles EO), and mixtures thereof.

The preferred formulation of the substrate-detergent blend to be used in a particular assay system depends upon several factors as follows:
1. The hydrophile-lipophile balance (HLB) of the nonionic detergents
2. The hydrophobicity of the substrate
3. The properties of the ester hydrolase to be measured
4. The properties of the liqid in which the ester hydrolase is found The specific activity of carboxylic acid ester hydrolases is partly affected by both the HLB and the total amount of the nonionic detergent present in the assay system. Since one role of the nonionic detergent in this invention is to help solubilize the substrate, for any water insoluble substrate there should be a minimum amount of nonionic detergent required to effect complete solubilization and to prevent dissolution upon standing. This minimum amount of nonionic detergent depends upon the water solubility of the substrate and the HLB of the nonionic detergent. Generally, the more hydrophobic substrates require more nonionic detergents for solubilization than the more hydrophilic substrates. The range of molar ratios of detergent to substrate that is useful in this invention is from about 1:1 and 10:1 (i.e. 5 to 150 mM of nonionic detergent) but about 1.50 to 5.00:1 is preferred. The lower the HLB of a detergent the more efficiently it will solubilize a hydrophobic substrate. The range of HLB's that is useful is from about 13 to 18, but about 14 to 16 is preferred. Two or more nonionic detergents may be blended together to produce a desired HLB. Generally, to obtain the highest specific activity of an ester hydrolase toward a particular substrate in this invention, one should endeavor to use as little nonionic detergent and as high an HLB as possible. Further, the source of the carboxylic ester hydrolase should be a consideration in determining the preferred substrate-detergent blend. For example, if blood serum of plasma is to be analyzed for ester hydrolase, a very lipemic serum may lead to turbidity changes of such long duration (>5 min.) that spectrophotometric analysis will be prohibited unless the proper substrate-detergent blend is used. For minimum interference from lipemic serum using the vinyl omega-phenyl octanoate as substrate, the range of detergent HLB that is useful is about 14 to about 18, but about 15 to 16 is preferred. The preferred range may differ when using other substrates.

As the second component of this reagent solution, a buffer solution which may contain certain activators and stabilizers is prepared. In the preparation of the buffer component, the following features must be taken into consideration:
(1) The pH of the buffer solution should be adjusted to match the pH optimum for the ester hydrolase to be measured. This is usually from about a pH of 6 to 10.
(2) The buffer used should have good buffering capacity at the pH used. Potassium phosphate is employed as the buffer for pH ranges of about 6 to 7.5, potassium pyrophosphate for pH ranges of about 6 to 9.5. The sodium salts may be used as well. Care must be taken to avoid using any buffer which has a primary amine group, e.g., tris (hydroxymethyl) amino methane, which will form a Schiff base with acetaldehyde, and thus interfere with the quantitation of acetaldehyde. An especially preferred buffer is N,N-bis(2-hydroxy-ethyl)glycine, sold under the trade name Bicine.
(3) The concentration of the buffer should be high enough to be effective on storage and to compensate for any acid or base that may be added along with the ester hydrolase. The buffer concentration range may be from about 0.05 Molar up to the limits of solubility, but most preferred is from 0.05 to M to 0.5 Molar.

In order to improve the sensitivity of the stable, clear reagent solution of this invention, enzyme activators may be included. Bile salts (or the corresponding bile acids) known in the prior art as activators for pancreatic lipase can be used as activators in the systems of this invention. Among those bile salts useful as activators in this invention, sodium taurodeoxycholate, sodium cholate, sodium chenodeoxycholate and sodium deoxycholate are preferred. Of these, sodium deoxycholate is the most preferred bile salt.

The range of concentrations of sodium deoxycholate (or its free acid) is from zero to about 25 mM, but the preferred range is about 15 to 21 mM for porcine pancreatic lipase, crude human pancreas extract, and lipase in human blood serum. Porcine liver esterase is only slightly activated by sodium deoxycholate concentrations up to about 25 mM. Sodium taurodeoxycholate from zero to 25 mM, sodium cholate from zero to 10 mM, and sodium chenodeoxycholate from zero to 15 mM all slightly activate porcine pancreatic lipase and porcine liver esterase to about the same extent using vinyl omega-phenyl octanoate as the substrate in this system, but the preferred concentrations in each case are approximately the upper limit of each range tested.

Activation of porcine pancreatic lipase and crude human pancreas extract can also be accomplished with various cationic alkyl and alkyl-aryl quaternary ammonium compounds such as cetyltrimethyl ammonium bromide (CTAB) and cetyldimethylbenzyl ammonium chloride (CDMBAC) in the absence of bile salts. The useful range of CTAB concentrations for activation of porcine pancreatic lipase is from about 4 to 12 mM, but most preferred is from 7 to 9 mM. The useful range of CDMBAC concentrations for activation of porcine pancreatic lipase is from about 2 to 9 mM, but most preferred is about 5 to 9 mM. When used together sodium deoxycholate (or its acid) and either CTAB or CDMBAC activate porcine pancreatic lipase about 10 fold over the activity without these components together. Sodium deoxycholate and CTAB are useful when used together in the ranges of zero to 25 mM and zero to 15 mM, respectively, but the preferred concentrations are 10 mM to 20 mM sodium deoxycholate and 4 mM to 10 mM CTAB. When deoxycholate and CDMBAC are used together for the activation of porcine pancreatic lipase the useful concentrations of deoxycholate are from zero to about 20 mM, but the preferred concentrations are 10 mM to 20 mM deoxycholate and 10 mM to 15 mM CDMBAC. Crude human pancreatic extract, also, shows an activation by a combination of deoxycholate and CDMBAC, in the concentration range of zero to 16 mM CDMBAC and zero to about 4 mM deoxycholate. When the deoxycholate concentration is about above 4 mM human lipase is activated to a much greater extent in the absence of CDMBAC.

Certain portein stabilizers can be added to the buffer solution. These include dithiocrythritol, dithiothreitol, serum albumin, ethylenediamine tetraacetic acid, and mercaptoethanol. Sulfhydral compounds are particularly useful in effecting the stabilization activity. Preferable stabilizers are dithioerythritol, dithiothreitol, and bovine serum albumin. For dithioerythritol or dithiothreitol the preferable concentration used in this invention is about $1 \times 10^{-3}$ M. These two stabilizers are quite similar and may be used interchangeably. For serum albumin stabilizers, the preferable concentration is from about 0.1% (w/v) to about 1.0% (w/v). If too much serum albumin is used, and if the ionic strength of the solution is very high, salting out of the protein may occur.

The ionic strength of the analysis system is important for optimum specific activity. Many triglyceride hydrolases have increased specific activity as the ionic strength increases. Other hydrolases are inhibited by increased ionic strength. This parameter may be adjusted to obtain the highest specificity of the assay for a particular hydrolase. Although a variety of neutral salts can presumably be used to increase the ionic strength of the reagent, KCl and NaCl are preferred. These compounds should be used from zero to about 3 M concentration, depending upon which carboxylic ester hydrolase is to be measured. The preferable concentration range in the reagent for the measurement of both porcine pancreatic lipase and human pancreatic lipase is from about 2.5 M to about 3.0 M. Porcine liver esterase is inhibited by increased ionic strength; therefore, it is preferable not to add neutral salts to the reagent for the measurement of this enzyme.

In order to monitor the formation of acetaldehyde produced by the enzymatic hydrolysis of the vinyl ester, a variety of analytic procedures can be employed. Enzymatic coupling systems consisting of an enzyme and its cofactor may easily be used for continuous monitoring of the action of the carboxylic ester hydrolase. Such enzyme-cofactor pairs may include alcohol dehydrogenase and $\beta$-dihydronic $\beta$inamide adenine dinucleotide (NADH), aldehyde dehydrogenase and $\beta$-nicotinamide adenine dinucleotide (NAD+) or $\beta$-nicotinamide adenine dinucleotide phosphate (NADP+), and aldehyde oxidase and either of the artificial electron acceptors 2, 6-dichlorophenolindophenol and cytochrome C. All of these aldehyde detection procedures are known to the prior art. The most preferred enzyme-cofactor pair is alcohol dehydrogenase and NADH. One advantage of detecting acetaldehyde by this means is that there is no net pH change in the overall reaction. The alcohol dehydrogenase is commercially available in crystallized form and is relatively inexpensive. The enzyme obtained from yeast has been used routinely in the systems of this invention and is preferred since it is the least expensive of any of the commercially available forms. Alcohol dehydrogenase from other sources may be used, also. The activity of the alcohol dehydrogenase, or any other coupling enzyme that is utilized, should be at least 10 times the highest activity of ester hydrolase that is added to the assay system to ensure that the measured activity is indeed due to the ester hydrolase activity and not to the coupling enzyme. The range of concentration of alcohol dehydrogenase employed for the analysis of about 50 ul of blood serum is from about 1 to 5 Units per milliliter of reagent.

The concentration of NADH must be high enough to saturate the ADH and to provide an assay of sufficient duration to obtain a true measurement of ester hydrolase activity. The useful range of NADH concentrations is from about 0.08 mg/ml to about 0.4 mg/ml. If the concentration is very much higher than 0.4 mg/ml, the initial absorbance at 340 nm may exceed the limits of some spectrophotometers. If the concentration is much lower than about 0.08 mg/ml, the alcohol dehydrogenase may not be saturated enough with NADH to give maximum activity. Typically, the absorbance at 340 nm of the reagent is read after addition of NADH to assure that enough of the compound is in the reduced form. The useful range of the initial absorbance after addition of NADH is from about 0.6 up to about 3.0. The upper limit usually depends upon the design limitations of the spectrophotometer. The preferred range of absorbance at 340 nm with a 1 cm light path is from about 1.0 to 2.0. A reagent solution with a total volume of 1.15 ml (including 50 ul serum) and an initial absorbance of 2.0 at 340 nm can assay an ester hydrolase activity from about 3.7 to 1200 mulliunits/ml serum with a preincubation time of 3 minutes and an incubation time of 2 minutes during which the absorbance is monitored. The lower limit of 3.7 mu/ml serum is based upon a sensitivity limit of 0.001 A per minute in the spectrophotometer. If higher activities are encountered then less serum or a diluted serum may be used.

Chemical methods for following the formation of acetaldehyde may be employed in place of the above-mentioned enzymatic coupling system. As a preferred method, acetaldehyde can be coupled with an amine to form a Schiff base: Such can be determined by standard spectrophotometer or fluorometric techniques.

The temperature at which the reagent is used may vary over a wide range as long as it is constant throughout the measurement. Temperatures of from about 0.0° C. to about 50° C. may be used in the analysis of this invention. Enzymatic assays are normally measured at 25° C., 30° C., or 37° C. While any of these temperatures can preferably be used for this reagent, 30° C. is recommended in accordance with the International Union of Pure and Applied Biochemistry recommendations for standardizing enzymatic assays. When the reagent in liquid form is stored the rate of spontaneous hydrolysis of the vinyl ester and, hence, NADH oxidation when the coupling system is present, depends upon the temperature of storage. The rates of NADH oxidation upon storage at 30° C., room temperature (23° C.), and ice temp. (4° C.) in a reagent with vinyl omega-phenyl octanoate as substrate in one experiment were 0.0262 μmole/hour, 0.0165 μmole/hour, and 0.0038 μmole/hour, respectively. In the case of a reagent whose absorbance at 340 nm is initially about 1.3, the useful life of the reagent, i.e., until the absorbance falls below 0.6, at 30°, 23°, and 4° C. is therefore 4.9, 7.8, and 33.9 hours, respectively. The pH of the reagent was 7.2. The usefullness of the reagent may be restored simply by adding more NADH.

It should be understood that while the reagent of this invention is manually prepared in the form of an aqueous solution, it is possible to subject the aqueous preparation to lyophilization and thereby form a dry powder reagent. Such can be activated by adding the required amount of water thereto.

Having generally described the invention, a more complete understanding can be obtained by reference to a certain specific example, which is provided herein for purposes of illustration only and is not intended to be limiting unless otherwise specified.

EXAMPLE

For the preparation of one liter of the reagent system for hydrolase activity determination, the following mixtures are formulated:

(1) Substrate-Detergent Blend. The method of mixing the substrate-detergent blend is not critical. One way in which such can be prepared is to mix 1.985 gm vinyl omega-phenyl octanoate with 9.081 gm 1, 1, 3, 3-tetramethyl-1-phenoxy (polyethoxy)$_n$ butane (n=polydisperse, average 9) and 9.133 gm of a 70% aqueous mixture of a similar compound where n=polydisperse, average 30. The resulting viscous mixture is mixed until homogeneous. A large quantity of this mixture may be prepared as desired and stored in a stoppered container indefinately at room temperature.

(2) Buffer Solution. While the method of preparation of the buffer solution is not critical, one method for forming it is as follows: Weigh into a one liter beaker 3.134 gm 1, 1, 3, 3-tetramethyl-1-phenoxy (polyethoxy) butane (n=polydisperse, average 9) and 12.912 gm 1, 1, 3, 3-tetramethyl-1-phenoxy (polyethoxy)$_n$ butane, 70% (n=polydisperse, average 30). Add about 800 ml of deionized or glass redistilled water and stir with a magnetic stirring bar until the detergents are dissolved. Add 9.534 gm sodium deoxycholate and continue stirring until dissolved. Then add 25.652 gm tetrasodium pyrophosphate (Na$_4$P$_2$O$_7$.10 H$_2$O) and stir until the crystals dissolve. Add with stirring in approximately five equal portions a total of 231.51 gm of potassium chloride, allowing each portion to almost completely dissolve before adding the next. Stop the stirring when all of the KCl has dissolved. Add 1.15 gm bovine serum albumin by sprinkling on the liquid surface. When all of the BSA has dissolved, begin stirring again and add more water to bring the volume up to about 950 ml. Adjust the pH to 9.1 with dilute HCl solution. Set the temperature compensation on the pH meter to the temperature at which the assays are to be run (30° C. in this example). Remove pH electrodes from the solution and add 0.1775 gm dithioerythritol with stirring. Quantitatively transfer the solution to a one liter volumetric flask and add water to the mark. Mix thoroughly. Into a one liter beaker combine the substrate-detergent blend and the buffer with stirring until thoroughly mixed. Add very slowly with stirring one milliliter of a yeast alcohol dehydrogenase solution containing 40 mg ADH/ml of a buffer with a similar composition as that described above. Filter the reagent through No. 402 filter paper (Carl Schleicher and Schuell Co.) to remove any insoluble foreign material. The reagent may be refrigerated in an unstoppered container, and portions aliquoted as needed for analyses. For example, to analyse one hundred serum samples for pancreatic lipase activity, remove a one hundred milliliter portion of the reagent. Add 30 mg NADH and stir until dissolved. After any endogenous acetaldehyde in the reagent has been reduced and the corresponding oxidation of NADH has slowed to the normal blank rate, the absorbance at 340 nm in a 1 cm light path will be approximately 1.5. One milliliter of the reagent and 0.1 ml water are pipetted into a suitable spectrophotometer cell and incubated at 30° C. for about 10 min. Then the cell is placed in a constant temperature (30° C.) cell compartment in a spectrophotometer and the change in absorbance at 340 nm is recorded on a calibrated chart recorder to obtain a blank rate. Fifty microliters of a serum is then added to the reagent, mixed by inversion a few times, and placed back into the cell compartment. The change in absorbance is again recorded on the chart recorder. The rate will usually become linear in less than three minutes after the serum addition. After a sufficient time to obtain a straight line of the absorbance change, calculate the net $\Delta$ A/min. by subtracting the blank rate from the rate after serum was added. The lipase activity in the serum is calculated as follows, using 6.22 A/cm. μmole as the extinction coefficient of NADH:

$\Delta$A/min. × 3698 = International Units Lipase/liter

An International Unit is defined as the conversion of one μmole of substrate per minute per liter of solution.

Having now fully described the invention, it will be apparent to one of ordinary skill in the art that many changes and modifications can be made thereto without departing from the spirit or scope of the invention as set forth herein.

What is claimed as new and intended to be covered by letters patent is

1. A stable, clear reagent solution for the analysis of carboxylic acid ester hydrolases which comprises a water insoluble vinyl ester of carboxylic acid, a nonionic detergent, a buffer, and neutral salts, wherein the value of the HLB of said detergent is from 13 to 18, said HLB value being chosen to obtain the highest specific activity for said ester hydrolase; wherein the ionic strength of said solution is adjusted by inclusion of said neutral salts to obtain the highest specific activity for said ester hydrolase; wherein the amounts of said ester, detergent and buffer, said HLB value and said ionic strength are chosen so that when said hydrolase is mixed with said reagent, the mixture is clear and has a stable spectrophotometric absorbance, and wherein said buffer is N,N-bis(2-hydroxy-ethyl)glycine.

2. The reagent solution of claim 1, wherein enzyme activators are added thereto and wherein said enzyme activators are selected from the group consisting of bile salts, bile acids, alkyl quaternary ammonium compounds, alkyl-aryl quaternary ammonium compounds and mixtures thereof.

3. The reagent solution of claim 2, wherein said enzyme activators are selected from the group consisting of deoxycholate acid, a salt of deoxycholate acid, cetyltrimethyl ammonium bromide, cetyldimethylbenzyl ammonium chloride and mixtures thereof.

4. The reagent solution of claim 2, wherein said vinyl ester of a carboxylic acid is selected from the group consisting of vinyl acetate, vinyl proprionate, vinyl butyrate, vinyl crotonate, vinyl valerate, vinyl hexanoate, vinyl octanoate, vinyl nonamoate, vinyl decanoate, vinyl neodecanoate, vinyl laurate, vinyl myristate, vinyl palmitate, vinyl oleate, vinyl stearate, divinyl suberate, vinyl omega-phenyl nonanoate and vinyl omega-phenyl octanoate.

5. The reagent solution of claim 2, wherein said nonionic detergent is selected from the group consisting of polyoxyethylenated alcohols, polyoxyethylenated alkylphenols, their ethers and mixtures thereof.

6. The reagent solution of claim 2, wherein said nonionic detergent is selected from the group consisting of polyoxyethylene (23) lauryl ether, polyoxyethylenated tert-octyl-phenol and mixtures thereof.

7. The reagent solution of claim 2, wherein said neutral salts are selected from the group consisting of potassium chloride, sodium chloride, and mixtures thereof.

8. The reagent solution of claim 2, wherein the concentration of said ester is from 5 to 15 mM; the concentration of said detergent is from 5 to 150 mM; the concentration of said buffer is from 0.05 up to the limit of solubility; and wherein the concentration of said neutral salt is from 0 to about 3 M.

9. The reagent solution of claim 2, wherein an acetaldehyde detection system is added thereto.

10. The reagent solution of claim 9, wherein said acetaldehyde detection system is enzymatic and is based upon the oxidation or reduction of said acetaldehyde with simultaneous reduction or oxidation, respectively, of a suitable electron donor or acceptor which can be measured spectrophotometrically or flurometrically.

11. The reagent solution of claim 10, wherein said enzymatic acetaldehyde detection system consists of alcohol dehydrogenase and $\beta$-dihydronicotinamide adenine dinucleotide (NADH), which are added in sufficient quantity to reduce said acetaldehyde to ethanol and oxidize said NADH to $\beta$-nicotinamide adenine dinucleotide (NAD+), whereby the rate of hydrolysis of said vinyl ester may be quantitated by the rate of disappearance of NADH.

12. The reagent solution of claim 9, wherein said acetaldehyde detection system is chemical and is based upon the combination of said acetaldehyde which an amine dye forming a colored Schiff base which can be determined spectrophotometrically or fluorometrically.

13. The reagent solution of claim 2, wherein said reagent solution is made to undergo lyophilization and results in a dry powdery agent.

* * * * *